United States Patent
Eberbach

[11] Patent Number: 5,810,753
[45] Date of Patent: Sep. 22, 1998

[54] GLOVE

[76] Inventor: Mark A. Eberbach, 4232 Winding Willow Dr., Tampa, Fla. 33624

[21] Appl. No.: 410,906

[22] Filed: Mar. 27, 1995

[51] Int. Cl.$^6$ ........................................................ A61F 5/00
[52] U.S. Cl. ................................ 602/21; 602/20; 602/63; 602/75
[58] Field of Search .................................. 473/61, 62, 63; 2/16, 17, 18, 19, 159–162; 602/20, 21, 22, 60, 62, 64, 262

[56] References Cited

U.S. PATENT DOCUMENTS

| | | |
|---|---|---|
| D. 263,073 | 2/1982 | Jonkers et al. ............................. D24/2 |
| 950,143 | 1/1910 | Sake . |
| 1,363,075 | 12/1920 | Adams . |
| 2,022,883 | 12/1935 | Gee . |
| 2,794,638 | 6/1957 | Etal . |
| 3,124,127 | 3/1964 | Ruuska . |
| 3,238,939 | 3/1966 | Stubbs . |
| 3,327,703 | 6/1967 | Gamm . |
| 3,512,776 | 5/1970 | Thomas . |
| 3,533,407 | 10/1970 | Smith . |
| 3,598,408 | 8/1971 | Klene . |
| 3,606,319 | 9/1971 | Borden . |
| 3,670,731 | 6/1972 | Harmon . |
| 3,707,730 | 1/1973 | Slider . |
| 3,710,790 | 1/1973 | Lemon . |
| 3,728,738 | 4/1973 | Andolino . |
| 3,815,908 | 6/1974 | Hashimoto . |
| 3,863,271 | 2/1975 | Moroney . |
| 3,942,535 | 3/1976 | Schulman . |
| 3,971,374 | 7/1976 | Wagner . |
| 4,005,709 | 2/1977 | Laerdal . |
| 4,022,197 | 5/1977 | Castiglia . |
| 4,040,632 | 8/1977 | Pawl . |
| 4,071,913 | 2/1978 | Rector . |
| 4,081,150 | 3/1978 | Tyson . |
| 4,183,098 | 1/1980 | Knowles, Jr. ............................... 21/16 |
| 4,190,054 | 2/1980 | Brennan . |
| 4,190,906 | 3/1980 | Patton, Jr. . |
| 4,309,991 | 1/1982 | DeMarco . |
| 4,366,812 | 1/1983 | Nuzzo . |
| 4,374,239 | 2/1983 | Norman . |
| 4,436,089 | 3/1984 | Schmid . |
| 4,441,490 | 4/1984 | Nirschl . |
| 4,470,417 | 9/1984 | Gruber . |
| 4,517,968 | 5/1985 | Greene . |
| 4,554,317 | 11/1985 | Behar . |
| 4,558,694 | 12/1985 | Barber . |
| 4,584,993 | 4/1986 | Nelson . |
| 4,747,163 | 5/1988 | Dzierson . |
| 4,748,975 | 6/1988 | Yashima . |
| 4,841,962 | 6/1989 | Berg . |
| 4,850,341 | 7/1989 | Fabry . |
| 4,852,556 | 8/1989 | Groiso . |
| 4,881,533 | 11/1989 | Teurlings . |
| 4,934,357 | 6/1990 | Frantzich . |
| 4,971,047 | 11/1990 | Kanzler . |
| 5,014,689 | 5/1991 | Meunchen . |
| 5,031,640 | 7/1991 | Spitzer ..................................... 128/878 |
| 5,058,573 | 10/1991 | Hess . |
| 5,065,752 | 11/1991 | Sessions . |
| 5,115,801 | 5/1992 | Cartmall . |
| 5,135,518 | 8/1992 | Vera ........................................ 604/291 |
| 5,267,943 | 12/1993 | Dancyger .................................. 602/5 |
| 5,335,888 | 8/1994 | Thomsen .................................. 248/11 |
| 5,350,418 | 9/1994 | Janevski ................................... 607/111 |
| 5,376,066 | 12/1994 | Phillips .................................... 602/21 |
| 5,397,296 | 3/1995 | Sydor ...................................... 602/21 |
| 5,409,591 | 4/1995 | Brinnand et al. .......................... 2/20 |
| 5,591,121 | 1/1997 | Cantrell .................................. 602/21 X |

Primary Examiner—Richard J. Apley
Assistant Examiner—Kim M. Lee
Attorney, Agent, or Firm—Stein, Schifino & Van Der Wall

[57] ABSTRACT

A device adapted to be worn by a user to protect an elongated portion of the user's body. The device comprises a support member positionable on a user's body adjacent to the elongated portion of the user's body to be protected. A pair of anatomically linear load-bearing members are included. The load-bearing members are coupled in laterally spaced relationship with respect to the support to define an elongated space therebetween. The load-bearing members and space therebetween are essentially parallel with each other and parallel with the elongated portion of the user's body to be protected. Further included are retention means to maintain the support member in position on the user's body with the space between the load-bearing members overlying the elongated portion of the user's body to be protected.

28 Claims, 6 Drawing Sheets

GLOVE

BACKGROUND OF THE INVENTION

1. Field of the Invention

This invention relates to a glove and, more particularly, to a glove adapted to be worn on the hand, distal forearm and wrist of a user for increased comfort and support.

2. Description of the Background Art

Carpal-tunnel syndrome is a significant problem in the work place. It is believed to occur from repetitive stress trauma. The theory is that frequent movement of the hand, excessive vibrations or other such trauma will result in disfunction of the median nerve. The theory addresses only one of the causes. In fact, the more significant problem, particularly with bench working individuals, such as typists, computer users, data processors and the like, is in the repetitive motion of the fingers in combination with direct pressure on the nerve caused by laying the wrist down upon the table or keyboard. Such combination of pressure with motion increases the friction injury to the nerve which compounds the problem.

By providing elements for off-loading forces from the median nerve to adjacent areas, areas that are less susceptible to pressure injury, it has been found possible to prevent and relieve the symptoms of carpal-tunnel syndrome and median nerve injury. The purpose of the present invention is to off-load the median nerve through a glove of a new, useful and unobvious design which also allows full and free motion of the wrist and hand.

As evidenced by a large number of prior art patents, efforts are continuing to improve gloves for various purposes. Consider, for example, U.S. Pat. No. 4,747,163 to Dzierson which relates to an improved glove for cyclists. Such glove comprises a flexible shell including a palm side, an outside, glove fingers and a glove thumb. Resilient padding is permanently secured to the palm side of the glove shell, and extends substantially from the heel of the palm side of the shell toward the glove fingers and across the crotch area between the glove index finger and the glove thumb. The padding comprises an elastomeric layer, a layer of fibrous batting, and an external layer.

Also consider U.S. Pat. No. 4,881,533 to Teurlings which relates to a versatile orthopedic variance wrist brace. Such brace is designed to support the wrist joint in excessive weight bearing activities such as gymnastics. It includes an adjustable, removable palmar base support, a pad which elevates the wrist in a support position reducing the extension angle at the wrist joint, thus relieving pressure and pain in the wrist. This palmar pad is designated specifically to compensate for imbalanced load forces which are the result of ulnar variance in support position at the wrist joint. The wrist brace is also made of a dorsal base support pad including an elongated reinforcing member that consists of a rigid material and a malleable material for comfort. This dorsal reinforcing member supports the wrist and the upper part of the hand in extension and might have two malleable side support members. A wrist strap extends from the dorsal base support, adheres to the palmar base support and is wrapped around the user's wrist to hold both base supports into place. Two straps extend from both top sides of the palmar base support to adhere its free ends to the dorsal base support on the back side of the hand. One of these straps contours the thumb and the shorter strap contours the little finger side of the hand.

Lastly, consider U.S. Pat. No. 5,376,066 to Phillips et al. relates to a glove for the treatment and/or prevention of carpal tunnel syndrome. This glove-like device is to be worn on the hand and wrist of a person. It comprises a sleeve formed of an elastomeric material, for example, neoprene, which stretches longitudinally as well as transversely and includes a palmar side, a dorsal side, a distal end portion, an intermediate portion, and a proximal end portion. The distal end portion of the sleeve includes respective finger receiving openings. A thumb receiving opening is provided in the intermediate portion of the sleeve. The proximal end of the sleeve includes a releasably securable strap located adjacent the wrist of the person for wrapping about a portion of the wrist to secure the glove-like device in place. When the device is in place the person's fingers extend through the respective finger openings and the person's thumb extends through the thumb opening. The dorsal side of said sleeve is biased backwards at a slight angle to the axis of the wearer's wrist for extending the wearer's hand in extension at that slight angle to the axis. The intermediate portion of the sleeve is configured to tightly encircle the palm and contiguous dorsal portion of the hand to resist the palm from spreading. A pad may be provided on the palmar side of the glove-like member at the interface of the intermediate portion and proximal end portion.

As will become evident, nothing in the prior art provides the benefits and advantages attendant with the present invention.

Accordingly, it is an object of this invention to provide an improvement which overcomes the aforementioned inadequacies of the prior art devices and provides an improvement which is a significant contribution to the advancement of the art.

Another object of this invention is to provide comfort and support to bench-top workers.

Another object of this invention is to off-load forces from the median nerve.

Another object of the invention is to abate carpal-tunnel syndrome.

Another object of this invention is to maintain full and unrestricted motion of the hand and wrist.

Another object of this invention is to provide a device adapted to be worn by a user to protect an elongated portion of the user's body. The device comprises a support member positionable on a user's body adjacent to the elongated portion of the user's body to be protected. A pair of anatomically linear load-bearing members are included. The load-bearing members are coupled in laterally spaced relationship with respect to the support to define an elongated space therebetween. The load-bearing members and space therebetween are essentially parallel with each other and parallel with the elongated portion of the user's body to be protected. Further included are retention means to maintain the support member in position on the user's body with the space between the load-bearing members overlying the elongated portion of the user's body to be protected.

The foregoing has outlined some of the pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

For the purpose of summarizing this invention, this invention comprises a new and improved device adapted to be worn on the hand, distal forearm and wrist of a worker manipulating a bench-top machine of the type including a computer mouse and a keyboard and the like. The device includes a tubular sleeve. The sleeve is in a generally cylindrical configuration when worn on the hand, distal forearm and wrist of a wearer and with a central axis adapted to be located in essentially parallel alignment with the median nerve of a wearer. The sleeve has an open proximal end positioned around the forearm of a wearer and an open distal end positionable around the hand of a wearer. The sleeve has a volar surface located between the ends and positionable over the palm of a hand, distal forearm and wrist of a wearer and a dorsal surface located between the ends and positionable over the back of a hand, distal forearm and wrist of a wearer. The sleeve has a radial region with a radial fold line located between the volar and dorsal surfaces and between the distal and proximal ends and an ulnar region with an ulnar fold line located between the volar and dorsal surfaces and between the proximal and distal ends. The radial and ulnar regions are at diametrically opposed locations and essentially parallel with the axis of the sleeve. The sleeve is fabricated of an elastomeric material having greater elasticity in the circumferential direction than in the axial direction. The sleeve has an axial length between the proximal and distal ends of between about four and eight inches with a circumference of between about four and ten inches. An opening in the radial region adjacent to the distal end is for the passage of a thumb of a wearer. A pair of elongated load-bearing members are secured to the volar surface. The load-bearing members are fabricated of a flexible and resilient material and have center lines positioned essentially parallel with each other and the axis of the sleeve. The support members are between about three and eight inches in length, ¼ and ⅜ inches in height, and ⅜ and ½ inches in width. The radial support member has a center line spaced between about ½ and 1 inch from the radial fold line and the ulnar support member has a center line spaced between about 1-¼ and 2-⅜ inches from the radial fold line. The support members have widely spaced exterior edges and closely spaced interior edges at a distance of between about ⅜ and 1 inch, and separated whereby when properly positioned on a wearer, the support members will be laterally offset from the median nerve of the wearer.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 16 is a further alternate embodiment illustrating a roll bar.

Similar reference characters refer to similar parts throughout the several Figures.

DETAILED DESCRIPTION OF THE PREFERRED EMBODIMENT

Figures 1, 6, 7:
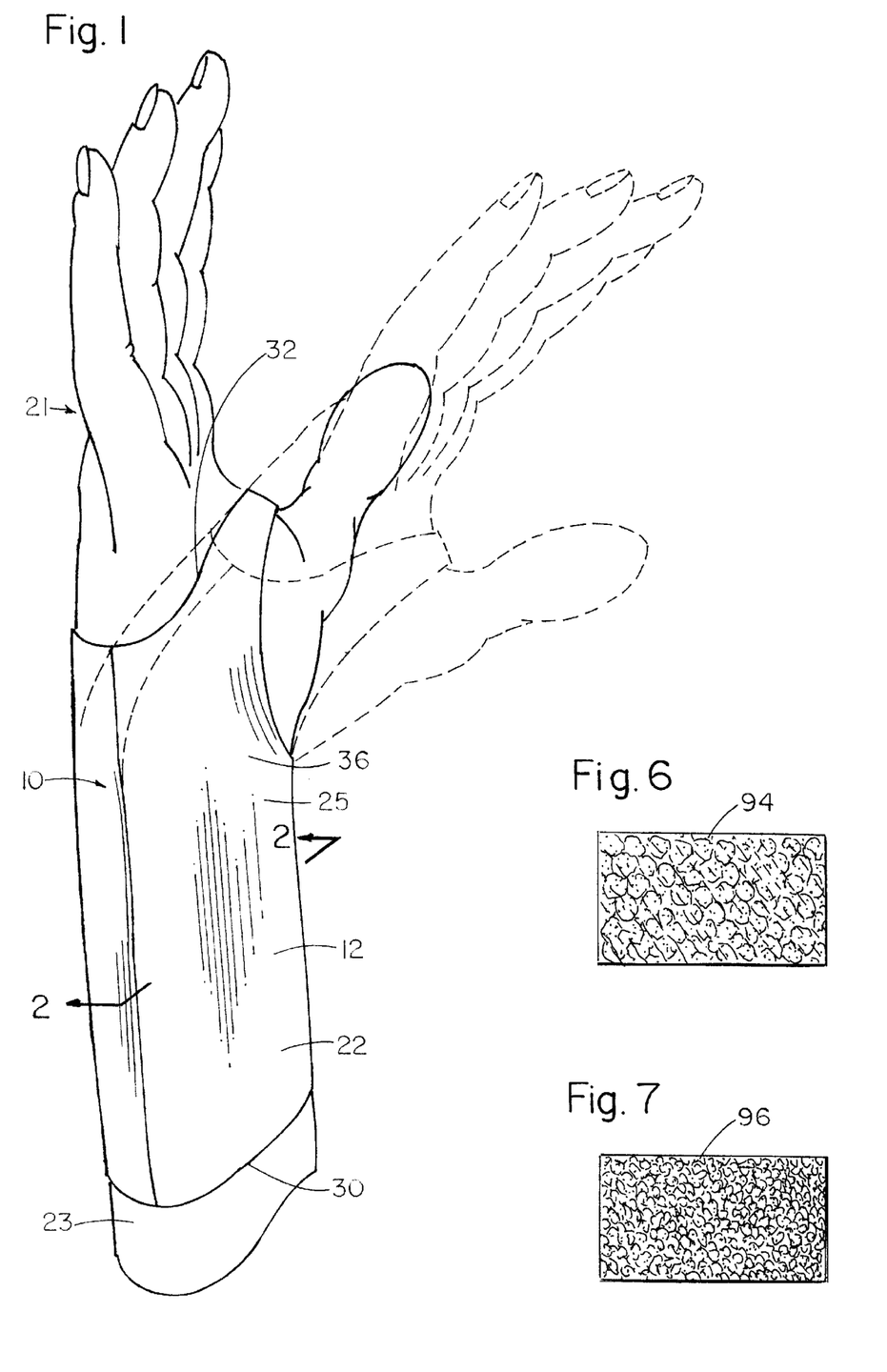
FIG. 1 is a perspective showing of the preferred embodiment of the new and improved glove shown on a hand, distal forearm and wrist of a wearer and constructed in accordance with the principles of the present invention with an alternate position shown in dotted lines.
FIGS. 6 and 7 are enlarged views of the foam in the load-bearing members of the glove shown in FIGS. 1 and 5.

With reference now to the drawings, and in particular to FIG. 1 thereof, there is shown a new and improved glove 10 constructed in accordance with the principles of the present invention. Such glove is comprised of a plurality of components. Such components in their broadest context include a support member 12 positionable on a user's body adjacent to the elongated portion of the user's body to be protected; a pair of anatomically linear load-bearing members 14 and 15 the load-bearing members being coupled in laterally spaced relationship with respect to the support to define an elongated space 16 therebetween, the load-bearing members and space therebetween being essentially parallel with each other and essentially parallel with the elongated portion of the user's body to be protected; and retention means 18 to maintain the support member in position on the user's body with the space between the load-bearing members overlying the elongated portion of the user's body to be protected. Such components are individually or jointly configured and correlated with respect to each other so as to attain the desired objective.

The primary component of the present invention is a tubular sleeve 22. The sleeve is in a generally cylindrical configuration. It takes the cylindrical configuration when worn on the hand 21, distal forearm 23 and wrist 25 of a wearer. When so configured on a wearer, a central axis 24 is formed. The central axis is adapted to be located in essentially parallel alignment with the median nerve 26 of the wearer.

The sleeve has an open proximal end 30 positioned around the forearm of a wearer. It also has an open distal end 32 positionable around the hand of a wearer.

In addition, the sleeve also has a volar surface 36. The volar surface is adapted to be located between the ends of the sleeve. Such volar surface is positionable over the palm of a hand, distal forearm and wrist of a wearer when in use. The sleeve also has a dorsal surface 38 located between the ends of the sleeve. The dorsal surface is positioned over the back of the hand, distal forearm and wrist of a wearer.

Located between the volar and dorsal surfaces is a radial region 42 which is adapted to form a radial fold line 43. The radial region is adjacent to the anatomically radial aspect of the hand, wrist and arm when worn and is located between the volar and dorsal surfaces as well as between the distal and proximal ends of the sleeve. Also included as a part of the sleeve is an ulnar region 44. The ulnar region has an ulnar fold line 45. Such fold lines are located between the volar and dorsal surfaces and extends between the proximal and distal ends of the sleeve. The radial and ulnar regions are at diametrically opposed locations around the circumference of the sleeve. They are located essentially parallel with the axis of the sleeve when the glove is worn.

In the preferred embodiment, the sleeve is fabricated of an elastomeric material. Such elastomeric material preferably has a greater elasticity in the circumferential direction than in the axial direction.

In the preferred embodiment, the sleeve has an axial length between the proximal and distal ends at the center thereof of between four and eight inches. The sleeve also has a circumference at its midpoint of between about four and eight inches. The size can vary as a function of the size of a user whether a child, woman, adult or extra-large. The elasticity of the sleeve allows for greater latitude in the sizing of the device to the user.

Next provided as a component of the system is an oval opening 48 in the radial region. This oval opening is adjacent to the distal end. Such opening functions for the passage of the thumb of a wearer. Such hole could also be formed as a simple linear slit 49 with the edges secured through stitching in the nature of a buttonhole.

Next provided as functioning components of the system are a pair of elongated load-bearing support members 14. Such members are secured to the volar surface of the sleeve. The support members are fabricated of a flexible material which is also resilient. The preferred material is closed-cell polyurethane foam.

Each of the load-bearing support members has its own individual center line 50 and 52. Such center lines are positioned essentially parallel with each other as well as essentially parallel with the axis of the sleeve. The support members are between three and eight inches in length. They are between 3/16 and 3/8 inches in height and are between about 3/8 and 5/8 inches in width. When utilized in the preferred mode, the radial support member center line is spaced between about 1/2 inch to one inch from the radial fold line and the ulnar support member center line is spaced between about one inch and 1-3/4 inches from the radial support member center line. When in use, they are separated whereby when properly positioned on a wearer, the support members will be laterally offset from the median nerve of a wearer by between about 3/16 and 3/8 inches. The support members having widely spaced exterior edges 54 and closely spaced interior edges 56 at a distance of between about 3/8 and 1 inch and are separated whereby, when properly positioned on a wearer, the support members will be laterally offset from the median nerve of the wearer.

Provided in an alternate embodiment of the invention is an arcuate recess 60. Such arcuate recess is formed in one edge of the radial support member. It is located adjacent to the radial region at the end thereof adjacent to the distal end. Such recess functions for the receipt of the base of the thumb (thenar eminence) of a wearer.

In the preferred embodiment of the invention, the elastomeric material of the sleeve is preferably elastic in all directions. A preferred elastic material for this purpose is spandex, preferably Raschel style spandex manufactured by Norbrook Industries, Ltd., New York, N.Y. Such material is characterized by the ability to elongate to different extents in different directions. In the preferred embodiment, it has been found that the preferred extent of elasticity is about 150 percent in the circumferential direction and about 50 percent in the axial direction. Such spandex fulfills such preferred capabilities. Spandex is a knitted fabric with the weaving being done by elastic strands. It is this arrangement which allows for the characteristics of the material of the present invention.

In one of the embodiments of the invention, the elastomeric material has a low coefficient of friction. Such is achieved by utilizing nylon strands when knitting the spandex.

In an alternate embodiment of the invention, the elastomeric material is of a relatively high coefficient of friction. Such is effected through the use of a less lubricous material such as cotton and wool.

In yet another embodiment of the invention, the volar surface 64 of the sleeve is fabricated of a wear-resistant material, preferably leather. Greater wear life is thus provided.

Figure 3:
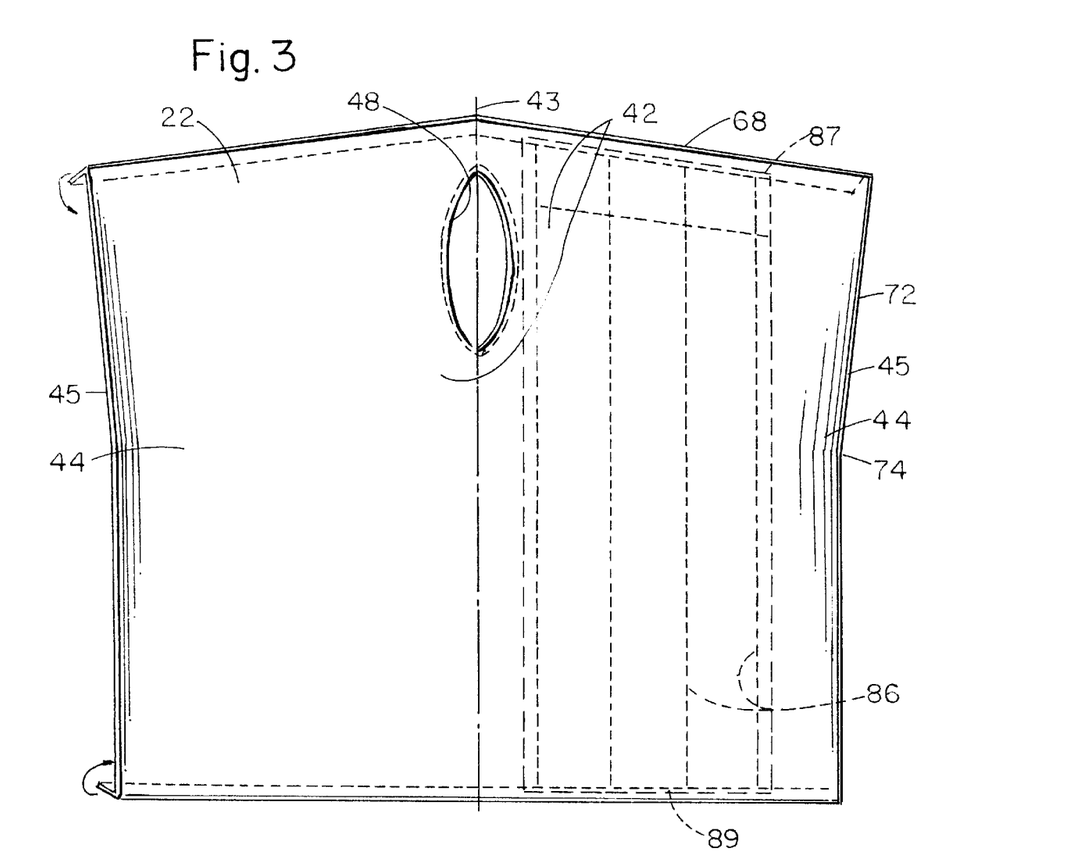
FIGS. 3 and 4 are plan views of the materials utilized to construct the sleeve showing such pieces of material in a planar orientation.
Figure 4:
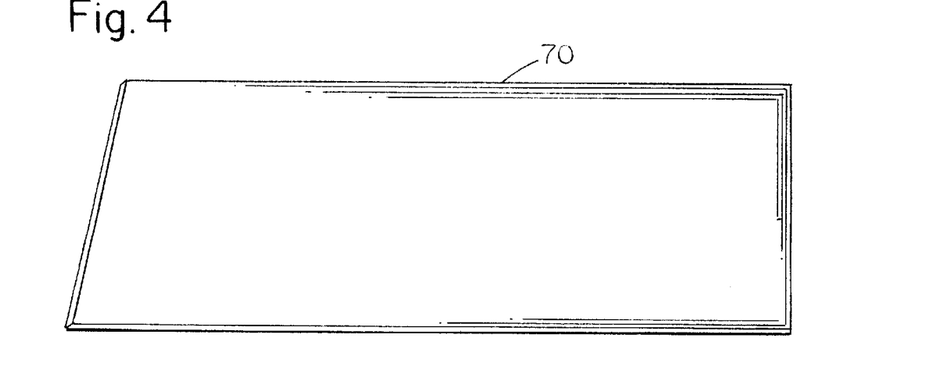

As can be seen in FIGS. 3 and 4, the materials 68 and 70 of which the present invention is utilized is laid out prior to stitching. An average size glove would be slightly larger than the sizes shown in order to allow bending over prior to stitching. Note that the material of the sleeve is formed with a gentle taper 72 angling downwardly toward the midpoint 74. This provides for a greater circumference of the sleeve at the distal end than at the proximal end. The circumference of the proximal end is essentially the same as that at the midpoint. The circumference at the proximal end may be greater than the circumference at the midpoint for certain application. Note is also taken that the length of the sleeve is greater at the radial fold line than at the ulnar fold line.

Figure 20:
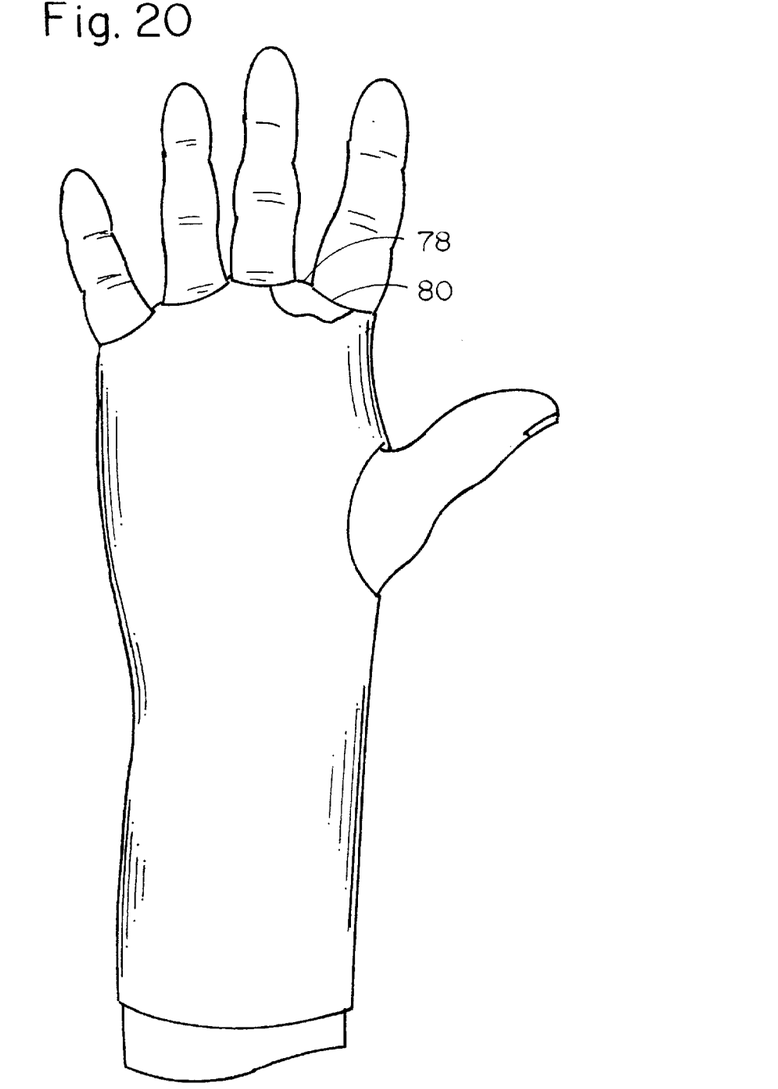
FIG. 20 is a perspective illustration of a further alternate embodiment of the invention.
Figure 21:
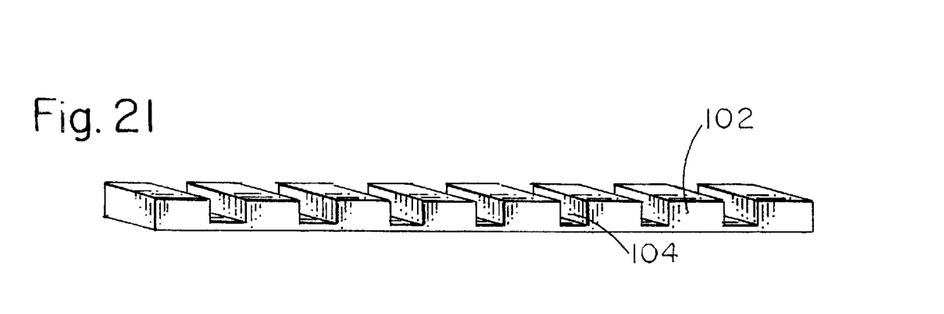
FIG. 21 is a perspective illustration of an additional alternate embodiment of a load-bearing member.

As can be seen in FIG. 20, the opening at the distal end is formed with spaced contact points formed as by stitches 78. Such contact points form therebetween a plurality of finger holes 80 for a wearer. In such embodiment, three such points of contact are provided for four finger holes to supplement the thumb hole. A lesser number of contact points could be utilized and strategically located so that more than one finger may pass through any one of the holes.

In the preferred embodiment of the invention, the load-bearing members are secured within pocket means 84 associated with respect to the sleeve. In the primary embodiment such pocket means is a single piece of fabric 70 with four parallel rows of stitching 86. This forms two side pockets, one for each support member. The pocket means may readily be formed of a common piece of material. The pocket means may also be formed of separate pieces of fabric. Such would require excess stitching and fabric piecing. An oblique stitch line 87 limits the pocket length to properly position the load bearing members. Openings 89 are at the proximal end of the sleeve and pockets for receiving and removing the load bearing members. Stitching 86 disposed axially hold the pocket material in place on the sleeve and form the pockets.

The pocket is preferably fabricated with a pocket segment material which is oriented with greater stretch in the axial direction and reduced stretch in the circumferential direction. This is to limit separation of the support members to insure their continued orientation in the proper anatomical position on the user. In such situation, the pocket and sleeve are fabricated of a common material but with the greater direction of stretch of the pocket material being at right angles to that of the sleeve. In such situation it is preferred to have the elastomeric material of the sleeve oriented to have maximum stretch around the circumference.

In yet another embodiment of the invention, the pocket segment may be sewn with simple stitching 90 to limit the lateral displacement of the load-bearing members with separation of the center line of the load-bearing members being about 1-¼ inch.

Consideration is now given with respect to the load-bearing members 14. Such load-bearing members are preferably made of an elastomeric foam, preferably a closed-cell polyurethane foam which will allow for greater ability in cleaning. Such load-bearing members are flexible to allow bending during operation and use. Such load-bearing members are also resilient to allow returning to their original shape after the removal of deforming forces.

In a yet further alternate embodiment of the invention, the load-bearing members are of variable compressibility to allow for easier flexing at the point where flexing normally occurs. This is readily effected through rendering the cells 94 of the foam of greater size in the area where the greater compressibility and flexibility is desired. Cells 96 are of a lesser size for lesser compressibility and flexibility.

In yet another alternate embodiment of the invention, the load-bearing members are segmented into a plurality of load-bearing members 102. In such embodiment, spacings 104 are provided along the center line of each of the load-bearing members.

Figures 2, 5, 8, 9, 10, 11:
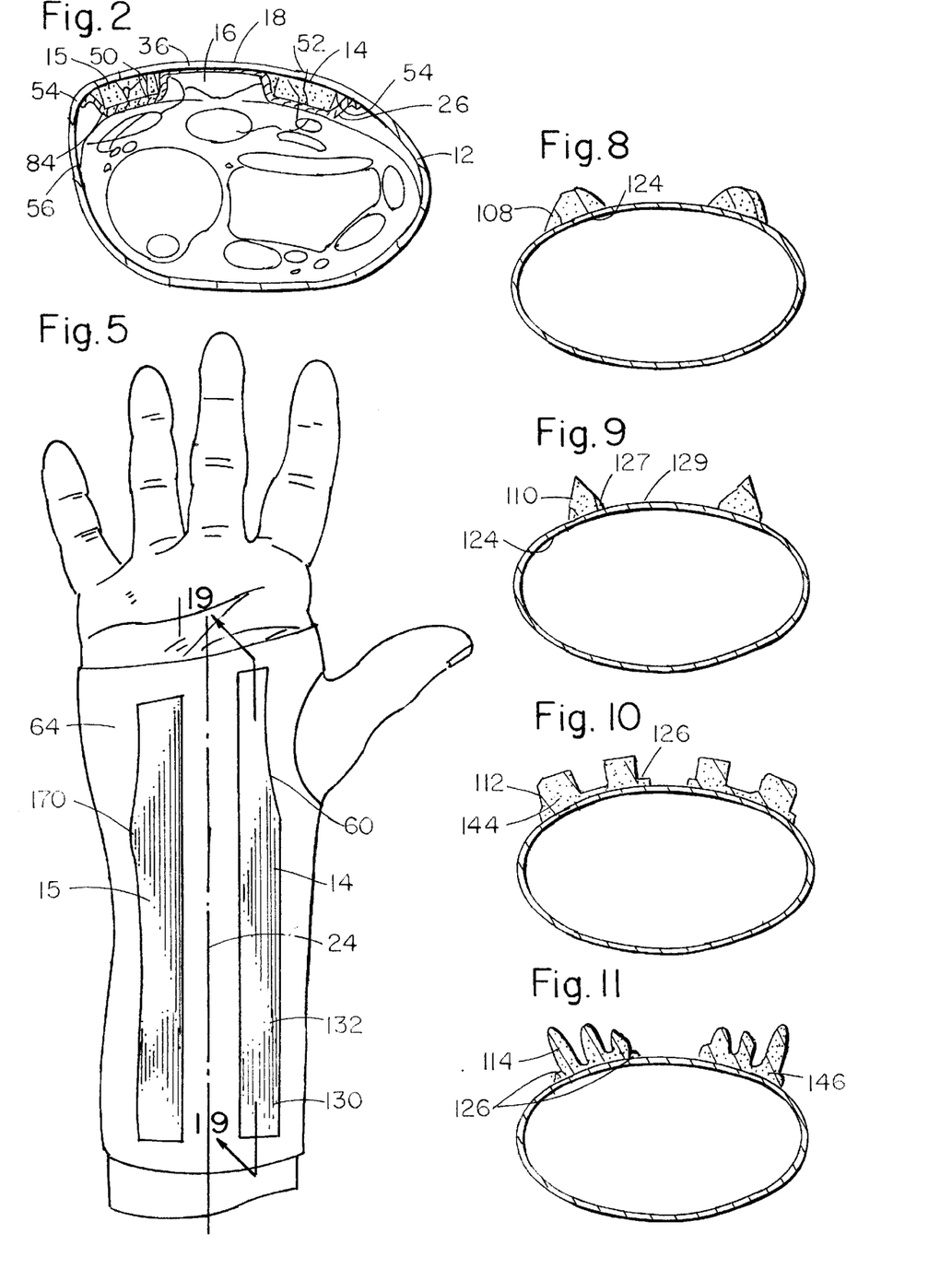
FIG. 2 is a cross-sectional view taken along line 2—2 of FIG. 1.
FIG. 5 is a front elevational view of a glove constructed in accordance with an alternate embodiment of the invention.
FIGS. 8 through 14 and 16 are cross-sectional views of the glove showing various alternate embodiments for the load-bearing members.

Varying cross-sectional configurations of the load-bearing members are shown in FIGS. 8 through 14. In FIG. 8, the load-bearing members 108 and 110 are tapered at the edges to conform flush to the plane of the sleeve.

Figure 12:
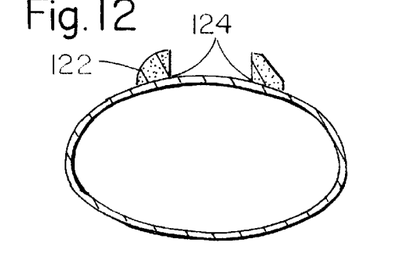
Figure 13:
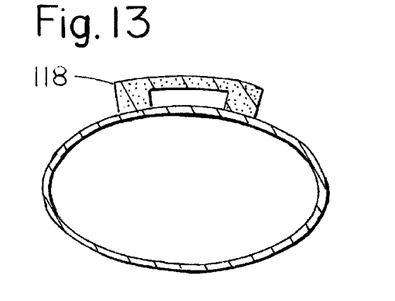
Figures 14, 15, 16, 17:
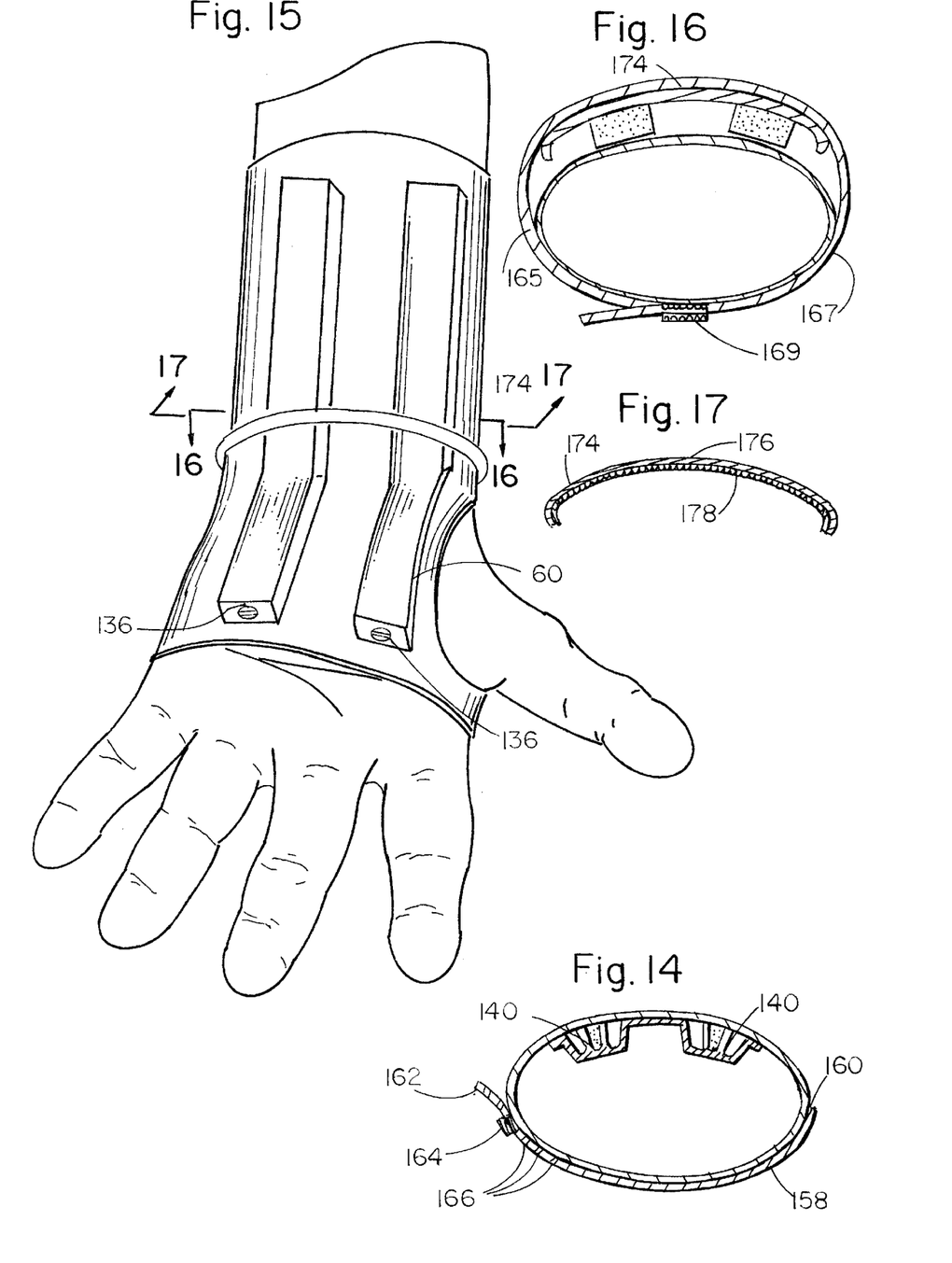
FIG. 15 is a perspective illustration of a glove constructed in accordance with an other alternate embodiment of the invention.
FIG. 17 is a cross-sectional view of the roll-bar taken along line 17—17 of FIG. 15.

Also shown in FIGS. 12, 13 and 14 are other alternate embodiments of the load-bearing members including the use of elongated parallel load-bearing members 112 and 114 which are greater than two in number.

In FIG. 13, there is shown an embodiment wherein the support members are connected by a transversely-oriented support member 118 external to the innermost plane of the sleeve.

In FIG. 12, the load-bearing members 122 are attached by glue 124. In FIG. 11, the load-bearing members are attached by stitching 126. In FIG. 9, the load-bearing members are removably coupled to the sleeve by complimentary sections of a pile-type fastener 128 and 128 such as Velcro.

In alternate embodiments of the invention the elongated load-bearing members may be tubes 130 filled with a cohesive gel 132. In the alternative, the load-bearing members may be tubes 134 which are simply inflated through valves 136 during operation and use.

In the preferred embodiment, the load-bearing members extend from about ½ inch proximal from the distal end to about ½ distal from the proximal end of the sleeve.

In any case, it is found that the preferred height of the support members must be at least ³⁄₁₆ of an inch for insuring a sufficient height to cause the off-loading of the median nerve.

A key feature of all of the embodiments is that the load-bearing members, regardless of their shape, have widely-spaced exterior edges in combination with closely-spaced interior edges. The interior edges are preferably at a distance of between about ⅜ inch and one inch. This allows for proper off loading of the median nerve.

In an alternate embodiment of the invention, the elongated segments 108 are shaped in cross-section as a hemi-ellipse. In another embodiment, the elongated segments 140 are shaped in cross-section such as a trapezoid. In yet another, the elongated segments 110 are shaped in cross-section as a triangle. Compare FIGS. 8, 14 and 9.

In the FIGS. 10 and 11 embodiments, the elongated segments are multiple members attached to a common base 144 and 146. As such, the segments are coupled together but at separated locations for effecting the off-loading of the median nerve.

Figure 18:
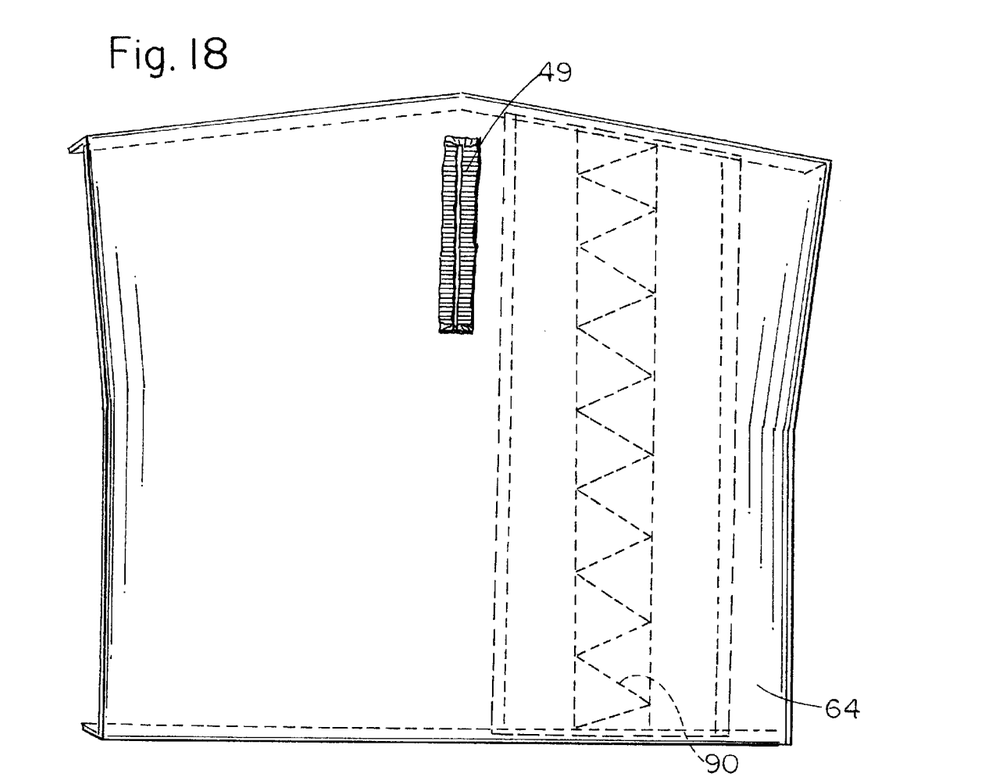
FIG. 18 is a plan view of a sleeve constructed in accordance with yet another alternate embodiment of the invention.
Figure 19:
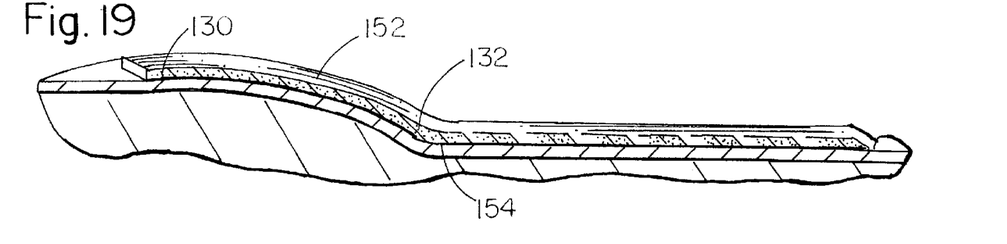
FIG. 19 is a cross-sectional view taken along line 19—19 of FIG. 5.

In a yet further embodiment of the invention, the load-bearing members 152 are fabricated of stiffened material. Such stiffened material includes a curvalinear bend 154 of between about fifteen and twenty-five degrees, preferably about twenty degrees located at a position adjacent to the mid-points 44 of the load-bearing members, perpendicular to the axis 24 of the sleeve. Such stiffened material in association with the bend tends to extend the wrist of a wearer dorsally for even further support. Such support may be fabricated of a stiffened material which is a laminated plastic. The stiffened material may also include an upper layer and a lower layer of different resistances. The stiffened material may be nylon or other plastic or, it may be a metal and, it might be of a molded material.

Another aspect of the present invention is the use of an adjustable strap 158 attached transverse to the axis of the sleeve. Such is shown in FIG. 14 as being located about the dorsal aspect of the mid-point 44 of the sleeve. The strap is secured at one end 160 at adjacent to the radial fold line and is releasably coupled at its other end 162 to a connector element laterally offset from adjacent to the ulnar fold line. Coupling and adjustment are effected through any appropriate means such as a button 164 and button hole 166. In an alternative embodiment, the single adjustment strap is replaced by two straps 165 and 167 stitched at opposite ends to the sleeve with a buckle 169 as one strap through which the other strap may pass for adjustment purposes. Note FIG. 16.

In an alternate embodiment of the invention, the elongated support member curves 60 to conform to the location of the thenar eminence of the hand.

Another feature of an alternate embodiment of the invention as shown in FIG. 5 is the elongated support member which is formed as by molding to include a lateral projection 170. Such projection is to conform and overlie the bony prominences of the wrist for added support.

FIGS. 15, 16 and 17 illustrate an optional roll bar 174 with a curved configuration secured to the exterior surfaces of the supporting members adjacent to their midpoints. Such roll bar facilitates rocking of the wearer's wrist for certain applications where such is desired. In FIG. 17, the roll bar is fabricated of two coupled strips 176 and 178 of metal of different degrees of elasticity to tailor the overall flexibility for the intended application.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A new and improved device adapted to be worn on the hand, distal forearm and wrist of a wearer manipulating a bench-top machine of the type including a computer mouse, a keyboard or the like, comprising, in combination:

a tubular sleeve, the sleeve being in a generally cylindrical configuration when worn on the hand, distal forearm and wrist of the wearer and with a central axis adapted to be located in essentially parallel alignment with the median nerve of the wearer, the sleeve having an open proximal end positioned around the forearm of the wearer and an open distal end positionable around the hand of the wearer, the sleeve having a volar surface located between the ends and positionable over the palm of a hand, distal forearm and wrist of the wearer and a dorsal surface located between the ends and positionable over the back of a hand, distal forearm and wrist of the wearer, the sleeve having a radial region with a radial fold line located between the volar and dorsal surfaces and between the distal and proximal ends and an ulnar region with an ulnar fold line located between the volar and dorsal surfaces and between the proximal and distal ends, the radial and ulnar regions being at diametrically opposed locations and essentially parallel with the axis of the sleeve;

the sleeve being fabricated of an elastomeric material having greater elasticity in the circumferential direction than in the axial direction;

the sleeve having an axial length between the proximal and distal ends of between about four and eight inches with a circumference of between about four and ten inches;

an opening in the radial region adjacent the distal end for the passage of a thumb of the wearer; and a pair of elongated load-bearing members secured to the volar surface, the load-bearing members being fabricated of a flexible and resilient material and having center lines positioned essentially parallel with each other and the axis of the sleeve, the load-bearing members being flexible in all directions off-axis from their respective center lines and along their respective lengths, the load-bearing members being between about three and eight inches in length, ¼ and ⅜ inches in height, and ⅜ and ½ inches in width, the radial load-bearing member having a center line spaced between about ½ and 1 inch from the radial fold line and the ulnar load-bearing member having a center line spaced between about 1-¼ and 2-⅜ inches from the radial fold line, the load-bearing members having widely spaced exterior edges and closely spaced interior edges at a distance of between about ⅜ and 1 inch, and separated whereby when properly positioned on the wearer, the load-bearing members will be laterally offset from the median nerve of the wearer.

2. A device adapted to be worn by a user to protect an elongated portion of the user's body comprising:

a support member positionable on a user's body adjacent to the elongated portion of the user's body to be protected;

a pair of anatomically linear load-bearing members, the load-bearing members being flexible in all directions off-axis from their respective center, lines and along their respective lengths, the load-bearing members being coupled in laterally spaced relationship with respect to the support to define an elongated space therebetween, the load-bearing members and space therebetween being essentially parallel with each other and parallel with the elongated portion of the user's body to be protected; and retention means to maintain the support member in position on the user's body with the space between the load-bearing members overlying, the elongated portion of the user's body to be protected, whereby when properly positioned on a wearer, the load-bearing members will be laterally offset from the median nerve of the wearer.

3. The device as set forth in claim 2 wherein the support member is fabricated of an elastomeric material which is elastic in all directions.

4. The device as set forth in claim 3 wherein the elastomeric material is spandex.

5. The device as set forth in claim 3 wherein the elastomeric material has a low coefficient of friction.

6. The device as set forth in claim 3 wherein the support member is a cylindrical sleeve with a volar surface which is of a wear-resistant material.

7. The device as set forth in claim 2 wherein the support member is an essentially cylindrical sleeve with a volar surface which is fabricated of leather.

8. The apparatus as set forth in claim 2 wherein the support member is an essentially cylindrical sleeve with a ulnar region and a radial region longer than the ulnar region.

9. The apparatus as set forth in claim 2 wherein the support member is a volar surface which is fabricated of a high coefficient of friction material.

10. The device as set forth in claim 2 wherein the support member is an essentially cylindrical sleeve which is gently tapered toward the mid-point with a greater circumference at a distal end than at a proximal end.

11. The apparatus as set forth in claim 2 and further including an arcuate recess formed in one edge of the support member adjacent to a radial region at the end thereof adjacent to the distal end for the receipt of the base of the thumb of a wearer.

12. The apparatus as set forth in claim 2 and further including a buttonhole formed in one corner of the support member adjacent to a radial region at the end thereof adjacent to the distal end for the receipt of the base of the thumb of a wearer.

13. The device as set forth in claim 2 and further including pocket means coupling the load-bearing members to the support member.

14. The device as set forth in claim 13 wherein the pocket means are fabricated of a fabric patch.

15. The device as set forth in claim 13 wherein the pocket means are fabricated of a plurality of fabric patches.

16. The glove as set forth in claim 13 wherein the pocket means is fabricated of a fabric patch oriented with greater stretch in the axial direction and reduced stretch along the circumference to limit the separation of the members.

17. The device as set forth in claim 2 wherein the support member is a sleeve with a pocket and the pocket and sleeve are both fabricated of material with the greater direction of stretch of the pocket material being at right angles to that of the sleeve's greater direction of stretch.

18. The device as set forth in claim 2 wherein the support member is fabricated of an elastomeric material in the form of a sleeve which is oriented to have maximal stretch along the circumference.

19. The device as set forth in claim 18 wherein the pocket segment is sewn to limit lateral displacement of the elongated support members.

20. The device as set forth in claim 2 wherein the load-bearing members are resilient.

21. The device as set forth in claim 2 wherein the load-bearing members are elastomeric foam.

22. The device as set forth in claim 2 wherein the load-bearing members are variable compressibility.

23. The device as set forth in claim 2 wherein the load-bearing members extend from about ¼ inch proximal from the distal end to ¼ inch distal from the proximal end of the sleeve.

24. The device as set forth in claim 2 wherein the load-bearing members include a radial load-bearing member which is longer than the ulnar load-bearing member.

25. The device as set forth in claim 2 wherein the load-bearing members are of a height of at least 3/16 inches, sufficient to cause the off-loading of the median nerve.

26. The device as set forth in claim 2 wherein the load-bearing members have widely spaced exterior edges and closely spaced interior edges being at a distance of between about ⅜ and one inch.

27. The device as set forth in claim 2 wherein the elongated load-bearing members are molded to conform to the bony prominences of the wrist.

28. The device as set forth in claim 2 wherein the support member is an essentially cylindrical sleeve with pocket material thereover coupled by axial stitch lines, a transverse stitch line at one end and an oblique stitch line at the other end.

* * * * *